(12) United States Patent
Pahan (10) Patent No.: US 12,239,637 B2
(45) Date of Patent: Mar. 4, 2025

(54) COMPOSITIONS AND METHODS FOR TREATING NEUROLOGICAL DISORDERS

(71) Applicant: Rush University Medical Center, Chicago, IL (US)

(72) Inventor: Kalipada Pahan, Skokie, IL (US)

(73) Assignee: RUSH UNIVERSITY MEDICAL CENTER, Chicago, IL (US)

( * ) Notice: Subject to any disclaimer, the term of this patent is extended or adjusted under 35 U.S.C. 154(b) by 186 days.

(21) Appl. No.: 17/968,264

(22) Filed: Oct. 18, 2022

(65) Prior Publication Data

US 2023/0046776 A1 Feb. 16, 2023

Related U.S. Application Data

(63) Continuation of application No. 16/958,903, filed as application No. PCT/US2018/067888 on Dec. 28, 2018, now Pat. No. 11,504,360.

(60) Provisional application No. 62/612,899, filed on Jan. 2, 2018.

(51) Int. Cl.
*A61K 31/439* (2006.01)
*A61K 9/00* (2006.01)
*A61K 31/4178* (2006.01)
*A61K 31/499* (2006.01)
*A61K 31/506* (2006.01)
*A61P 25/16* (2006.01)

(52) U.S. Cl.
CPC .......... *A61K 31/439* (2013.01); *A61K 9/0019* (2013.01); *A61K 9/0053* (2013.01); *A61K 31/4178* (2013.01); *A61K 31/499* (2013.01); *A61K 31/506* (2013.01); *A61P 25/16* (2018.01)

(58) Field of Classification Search
CPC .................................................. A61K 31/439
See application file for complete search history.

(56) References Cited

U.S. PATENT DOCUMENTS

| 11,504,360 | B2 * | 11/2022 | Pahan .................. A61K 31/499 |
| 2013/0116215 | A1 | 5/2013 | Coma et al. |
| 2014/0057940 | A1 | 2/2014 | Mankowski et al. |
| 2014/0357656 | A1 | 12/2014 | Zhang et al. |
| 2017/0184612 | A1 | 6/2017 | Sulzer et al. |

OTHER PUBLICATIONS

Brahmachari, S., and K. Pahan. 2010. Gender-specific expression of beta1 integrin of VLA-4 in myelin basic protein-Primed T cells: implications for gender bias in multiple sclerosis. J Immunol 184:6103-6113.
Brochard, V., B. Combadiere, A. Prigent, Y. Laouar, A. Perrin, V. Beray-Berthat, 0. Bonduelle, D. Alvarez-Fischer, J. Callebert, J.M. Launay, C. Duyckaerts, R. A. Flavell, E. C. Hirsch, and S. Hunot. 2009. Infiltration of CD4+ ymphocytes into the brain contributes to neurodegeneration in a mouse model of Parkinson disease. J Clin Invest 119:182-192.
Chabot, S., D. Charlet, T. L. Wilson, and V. W. Yong. 2001. Cytokine production consequent to T cell-microglia interaction: the PMNIFN gamma-treated U937 cells display similarities to human microglia. J Neurosci Methods 05:111-120.
Chandra, G., A. Roy, S. B. Rangasamy, and K. Pahan. 2017. Induction of Adaptive Immunity Leads to Nigrostriatal Disease Progression in MPTP Mouse Model of Parkinson's Disease. J Immunol 198:4312-4326.
Chandra, G., S. B. Rangasamy, A. Roy, J. H. Kordower, and K. Pahan. 2016. Neutralization of RANTES and Eotaxin Prevents the Loss of Dopaminergic Neurons in a Mouse Model of Parkinson Disease. J Biol Chem 291:15267-15281.
Dasgupta, S., M. Jana, X. Liu, and K. Pahan. 2002. Myelin basic protein-primed T cells induce nitric oxide synthase in microglial cells. Implications for multiple sclerosis. J Biol Chem 277:39327-39333.
Dasgupta, S., M. Jana, X. Liu, and K. Pahan. 2003. Role of very-late antigen-4 (VLA-4) in myelin basic protein-primed T cell contact-induced expression of proinflammatory cytokines in microglial cells. J Biol Chem 278:22424-22431.
Dauer, W., and S. Przedborski. 2003. Parkinson's disease: mechanisms and models. Neuron 39:889-909.
Dehmer, T., J. Lindenau, S. Haid, J. Dichgans, and J.B. Schulz. 2000. Deficiency of inducible nitric oxide synthase protects against MPTP toxicity in vivo. J Neurochem 74:2213-2216.
Emborg, M. E., P. Shin, B. Roitberg, J. G. Sramek, Y. Chu, G. T. Stebbins, J. S. Hamilton, P. D. Suzdak, J.P. Steiner, iind J. H. Kordower. 2001. Systemic administration of the immunophilin ligand GPI 1046 in MPTP-treated monkeys. Exp Neurol 168:171-182.
Gao, H. M., B. Liu, W. Zhang, and J. S. Hong. 2003. Novel anti-inflammatory therapy for Parkinson's disease. Trends Pharmacol Sci 24:395-401.
Gendelman, H. E., and R. L. Mosley. 2015. A Perspective on Roles Played by Innate and Adaptive Immunity in the Pathobiology of Neurodegenerative Disorders. J Neuroimmune Pharmacol 10:645-650.
Ghosh, A., A. Roy, J. Matras, S. Brahmachari, H. E. Gendelman, and K. Pahan. 2009. Simvastatin inhibits the iictivation of p21ras and prevents the loss of dopaminergic neurons in a mouse model of Parkinson's disease. J Neurosci 29:13543-13556.
Ghosh, A., A. Roy, X. Liu, J. H. Kordower, E. J. Mufson, D. M. Hartley, S. Ghosh, R. L. Mosley, H. E. Gendelman, and K. Pahan. 2007. Selective inhibition of NF-kappaB activation prevents dopaminergic neuronal loss in a mouse model of Parkinson's disease. Proc Natl Acad Sci US A 104:18754-18759.
Gibbs, R.A., et al., Evolutionary and Biomedical Insights from the Rhesus Macaque Genome, The Rhesus Macaque Genome, Research Article, Apr. 13, 2007, Science vol. 316, 222, www.sciencemag.org; DOI: 10.1126/science.1139247.

(Continued)

*Primary Examiner* — Rei Tsang Shiao (57) ABSTRACT

The present invention generally relates to compositions and methods for treating a neurological disorder in a subject, the method including administering to the subject in need of such treatment a composition including a therapeutically effective amount of a CCR5 antagonist. The CCR5 antagonist may be, for example, maraviroc. The neurological disorder may be, for example, Alzheimer's disease, Parkinson's disease, dementia with Lewy bodies or multiple system atrophy.

14 Claims, 9 Drawing Sheets

(56) References Cited

OTHER PUBLICATIONS

Gilliam, B. L., D. J. Riedel, and R. R. Redfield. 2011. Clinical use of CCR5 inhibitors in HIV and beyond. J Transl Med 9 Suppl 1:S9.
Goedert, M. 2001. Alpha-synuclein and neurodegenerative diseases. Nat Rev Neurosci 2:492-501.
Hunot, S., and E. C. Hirsch. 2003. Neuroinflammatory processes in Parkinson's disease. Ann Neural 53 Suppl 3:S49-58; discussion S58-60.
Iwasaki, A., and R. Medzhitov. 2010. Regulation of adaptive immunity by the innate immune system. Science 327:291-295.
Iwasaki, A., and R. Medzhitov. 2015. Control of adaptive immunity by the innate immune system. Nat Immunol 16:343-353.
Jana, M., S. Dasgupta, X. Liu, and K. Pahan. 2002. Regulation of tumor necrosis factor-alpha expression by CD40 ligation in BV-2 microglial cells. J Neurochem 80:197-206.
Jana, M., X. Liu, S. Koka, S. Ghosh, T. M. Petro, and K. Pahan. 2001. Ligation of CD40 stimulates the induction of nitric-oxide synthase in microglial cells. J Biol Chem 276:44527-44533.
Kannarkat, G. T., J. M. Boss, and M. G. Tansey. 2014. The role of innate and adaptive immunity in Parkinson's isease. J Parkinsons Dis 3:493-514.
Khasnavis, S., A. Roy, S. Ghosh, R. Watson, and K. Pahan. 2014. Protection of dopaminergic neurons in a mouse model of Parkinson's disease by a physically-modified saline containing charge-stabilized nanobubbles. J Neuroimmune Pharmacol 9:218-232.
Khasnavis, S., and K. Pahan. Sodium Benzoate, a Metabolite of Cinnamon and a Food Additive, Upregulates Neuroprotective Parkinson Disease Protein DJ-1 in Astrocytes and Neurons. J Neuroimmune Pharmacol 7:424-435.
Kordower, J. H., C. D. Herzog, B. Dass, R. A. Bakay, J. Stansell, 3rd, M. Gasmi, and R. T. Bartus. 2006. Delivery of neurturin by AAV2 (CERE-120)-mediated gene transfer provides structural and functional neuroprotection and neurorestoration in MPTP-treated monkeys. Ann Neurol 60:706-715.
Kordower, J. H., M. E. Emborg, J. Bloch, S. Y. Ma, Y. Chu, L. Leventhal, J. McBride, E. Y. Chen, S. Palfi, B. Z. R. pitberg, W. D. Brown, J. E. Holden, R. Pyzalski, M. D. Taylor, P. Carvey, Z. Ling, D. Trono, P. Hantraye, N. Deglon, nd P. Aebischer. 2000. Neurodegeneration prevented by lentiviral vector delivery of GDNF in primate models of Parkinson's disease. Science 290:767-773.
Lashuel, H. A., C.R. Overk, A. Oueslati, and E. Masliah. 2013. The many faces of alpha-synuclein: from structure and toxicity to therapeutic target. Nat Rev Neurosci 14:38-48.
Laurie, C., A. Reynolds, 0. Coskun, E. Bowman, H. E. Gendelman, and R. L. Mosley. 2007. CD4+ T cells from Copolymer-1 immunized mice protect dopaminergic neurons in the 1-methyl-4-phenyl-1,2,3,6-tetrahydropyridine model of Parkinson's disease. J Neuroimmunol 183:60-68.
Mogi, M., M. Harada, H. Narabayashi, H. Inagaki, M. Minami, and T. Nagatsu. 1996. Interleukin (IL)-1 beta, IL-2, IL-4, IL-6 and transforming growth factor-alpha levels are elevated in ventricular cerebrospinal fluid in juvenile parkinsonism and Parkinson's disease. Neurosci Lett 211:13-16.
Mondal, S., A. Roy, A. Jana, S. Ghosh, J. H. Kordower, and K. Pahan. 2012. Testing NF-kappaB-based therapy in hemiparkinsonian monkeys. J Neuroimmune Pharmacol 7:544-556.
Nagatsu, T., M. Magi, H. Ichinose, and A. Togari. 2000. Changes in cytokines and neurotrophins in Parkinson's disease. J Neural Transm Suppl:277-290.
Nitsch, R., E. E. Pohl, A. Smorodchenko, C. Infante-Duarte, O. Aktas, and F. Zipp. 2004. Direct impact of T cells on neurons revealed by two-photon microscopy in living brain tissue. J Neurosci 24:2458-2464.
Olanow, C. W., and W. G. Tatton. 1999. Etiology and pathogenesis of Parkinson's disease. Annu Rev Neurosci a2:123-144.
Qureshi, G. A., S. Baig, I. Bednar, P. Sodersten, G. Forsberg, and A. Siden. 1995. Increased cerebrospinal fluid concentration of nitrite in Parkinson's disease. Neuroreport 6:1642-1644.
Roy, A., A. Ghosh, A. Jana, X. Liu, S. Brahmachari, H. E. Gendelman, and K. Pahan. 2012. Sodium phenylbutyrate controls neuroinflammatory and antioxidant activities and protects dopaminergic neurons in mouse models of Parkinson's disease. PLoS One 7:e38113.
Roy, A., and K. Pahan. Prospects of statins in Parkinson disease. Neuroscientist 17:244-255.
Roy, A., S. Mondal, J. H. Kordower, and K. Pahan. 2015. Attenuation of microglial RANTES by NEMO-binding domain Deptide inhibits the infiltration of CD8(+) T cells in the nigra of hemiparkinsonian monkey. Neuroscience 302:36-46.
Sulzer, D., R. N. Alcalay, F. Garretti, L. Cote, E. Kanter, J. Agin-Liebes, C. Liang, C. McMurtrey, W. H. Hildebrand, X. Mao, V. L. Dawson, T. M. Dawson, C. Oseroff, J. Pham, J. Sidney, M. B. Dillon, C. Carpenter, D. Weiskopf, E. Phillips, S. Mallal, B. Peters, A. Frazier, C. S. Lindestam Arlehamn, and A. Sette. 2017. T cells from patients with Parkinson's disease recognize alpha-synuclein peptides. Nature 546:656-661.
Tanabe, Y., S. Sasaki, N. Mukaida, and T. Baba. 2016. Blockade of the chemokine receptor, CCR5, reduces the growth of orthotopically injected colon cancer cells via limiting cancer-associated fibroblast accumulation. Oncotarget 7:48335-48345.
Tang, P., L. Chong, X. Li, Y. Liu, P. Liu, C. Hou, and R. Li. 2014. Correlation between serum RANTES levels and the severity of Parkinson's disease. Oxid Med Cell Longev 2014:208408.
Velasco-Velazquez, M., W.Xolalpa, and R G. PesteIL 2014. The potential to target CCL5/CCR5 in breast cancer. Expert Opin Ther Targets 18:1265-1275.
Velasco-Velazquez, M., X. Jiao, M. De La Fuente, T. G. Pestell, A. Ertel, M. P. Lisanti, and R. G. Pestell. 2012. CCR5 antagonist blocks metastasis of basal breast cancer cells. Cancer Res 72:3839-3850.
Vila, M., and S. Przedborski. 2004. Genetic clues to the pathogenesis of Parkinson's disease. Nat Med 10 Suppl: S58-62.
Volpicelli-Daley, L.A., K. c. Luk, and v. M. Lee. 2014. Addition of exogenous alpha-synuclein preformed fibrils to primary neuronal cultures to seed recruitment of endogenous alpha-synuclein to Lewy body and Lewy neurite-like aggregates. Nat Protoc 9:2135-2146.
Wu, D. C., v. Jackson-Lewis, M. Vila, K. Tieu, P. Teismann, C. Vadseth, D. K. Choi, H. Ischiropoulos, and S. Przedborski. 2002. Blockade of microglial activation is neuroprotective in the 1-methyl-4-phenyl-1,2,3,6-xetrahydropyridine mouse model of Parkinson disease. J Neurosci 22:1763-1771.
Zi, J_, S. Yuan, J_ Qiao, K. Zhao, L. Xu, K_ Qi, K_ Xu, and L. Zeng_ 2017_ Treatment with the C—C chemokine receptor type 5 (CCR5)-inhibitor maraviroc suppresses growth and induces apoptosis of acute lymphoblastic leukemia cells. Am J Cancer Res 7:869-880.
International Search Report, issued in PCT/US2018/067888, dated Mar. 27, 2019.
International Preliminary Report on Patentability, issued in PCT/US2018/067888, dated Jul. 7, 2020.

* cited by examiner

COMPOSITIONS AND METHODS FOR TREATING NEUROLOGICAL DISORDERS

RELATED APPLICATIONS

This application is a continuation of U.S. application Ser. No. 16/958,903, filed Jun. 29, 2020, which is a National Stage application of International Application No. PCT/US2018/067888, filed Dec. 28, 2018, which claims the benefit of the filing date of U.S. Provisional Patent Application No. 62/612,899 filed Jan. 2, 2018, the contents of all of which are herein incorporated by reference.

STATEMENT AS TO RIGHTS TO INVENTIONS MADE UNDER FEDERALLY SPONSORED RESEARCH AND DEVELOPMENT

This study was supported by grants from the National Institutes of Health (R01 NS083054 and R21 NS064564). The Federal Government has certain rights in this invention.

TECHNICAL FIELD

The present invention generally relates to compositions and methods for treating a neurological disorder in a subject, the method including administering to the subject in need of such treatment a composition including a therapeutically effective amount of a CCR5 antagonist. The CCR5 antagonist may be, for example, maraviroc. The neurological disorder may be, for example, Alzheimer's disease, Parkinson's disease, dementia with Lewy bodies or multiple system atrophy.

BACKGROUND

Parkinson's disease (PD) is a neurodegenerative disorder that is characterized by tremor, bradykinesia, rigidity, and postural instability (1, 2). Pathologically, it is characterized by gliosis and progressive degeneration of the DA neurons associated with the presence of intracytoplasmic inclusions (Lewy bodies) in the substantia nigra pars compacta (SNpc) (3).

Although the etiology of PD is poorly understood, recent studies indicate that PD is regulated by the adaptive arm of the immune system (4-11). According to Brochard et al (8), both CD8+ and CD4+ T cells significantly invade the SNpc of PD patients and MPTP-intoxicated mice. We have also found the infiltration of both CD8+ and CD4+ T cells into the nigra of hemiparkinsonian monkeys (12). Although the contribution of each of these cell types in nigrostriatal degeneration is not yet known, removal of CD4+, but not of CD8+, T cells in mice greatly reduces MPTP-induced nigrostriatal dopamine cell death (8). While Th17 cells exacerbate nigrostriatal dopaminergic neurodegeneration, regulatory T cells have been shown to attenuate such neurodegeneration (9). Mechanisms by which T cells infiltrate into the CNS under neurodegenerating conditions are poorly understood.

At present, no effective therapy is available to halt the progression of PD. Carbidopa-Levodopa (Sinemet®) and/or a dopamine agonist has been the standard treatment for PD. However, it is often associated with a number of side effects and unsatisfactory outcomes. For example, after 2 years of therapy with Sinemet®, 30-50% of patients begin to experience dopaminergic-related complications, including dyskinesis, wearing off, or on-off motor fluctuations. These motor complications eventually influence the clinical picture. Therefore, developing an effective therapeutic approach to halt the progression of PD is of paramount importance. Numerous studies have been carried out in rodents on the role of innate and adaptive immune responses in PD (4, 29-34). However, there is a wide immunological gap between inbred rodent strains and heterogeneous human population. As a result, sometimes rodent results are not translated to humans. On the other hand, rhesus monkeys are old world monkeys and both rhesus monkeys and human are thought to have diverged from a common ancestor, a primitive anthropoid, approximately 25 million years ago. Interestingly, despite 25 million years of evolutionary separation, humans and macaques apparently share about 93% of their DNA sequence (35). It is also important to note that the immune systems of rhesus monkeys and humans are very similar, suggesting that in situations, where it is desirable, but impossible, to study human neuroimmune responses in vivo, rhesus monkey provides the best available alternative.

Maraviroc (Selzentry®) is an FDA-approved drug for treating HIV infection. This drug is also currently being explored for treating different cancer (36, 37). Recent studies have shown that maraviroc suppresses the metastasis of breast cancer (38) in different models. One clinical trial is also underway to study the efficacy of maraviroc in metastatic colorectal cancer.

SUMMARY OF THE PREFERRED EMBODIMENTS

The present invention generally relates to a method for treating a neurological disorder in a subject. The subject may be a human subject. In one embodiment, the method includes administering to the subject in need of such treatment a composition including a therapeutically effective amount of a CCR5 antagonist. In various embodiments, the CCR5 antagonist is maraviroc, aplaviroc, cenicriviroc or vicriviroc. In one preferred embodiment, the CCR5 antagonist is maraviroc.

In one embodiment, the neurological disorder is characterized by an upregulation of at least one of the RANTES and eotaxin chemokines. The neurological disorder may be, for example, Alzheimer's disease, Parkinson's disease, dementia with Lewy bodies and multiple system atrophy.

In another embodiment, the composition also includes at least one pharmaceutically acceptable carrier. In yet another embodiment, the composition is administered orally. In another embodiment, the composition is administered by a subcutaneous, intra-articular, intradermal, intravenous, intraperitoneal or intramuscular route.

In various embodiment, the CCR5 antagonist is administrated orally in a daily amount of less than 200, 10, or 1 mg/kg body weight of the human subject.

BRIEF DESCRIPTION OF THE DRAWINGS

FIG. 2 (A-E). Oral maraviroc treatment inhibits the infiltration of CD4+ T cells into the nigra of hemiparkinsonian monkeys. Naïve female rhesus monkeys received a right intracarotid injection of MPTP. After 7 d of injection, monkeys displaying classical parkinsonian postures received maraviroc (1 mg/kg body wt/d) orally mixed with banana. MPTP group of monkeys also received normal banana as control. After 30 d of treatment, ventral midbrain sections were DAB-stained for CD4 (A, vessel; B, parenchyma). C) Sections were double-labeled for CD4 and TH. CD4-positive cells were counted in two nigral sections (D, within 100 μm around vessel; E, parenchyma within 100 to 200 μm around vessel) of each of four monkeys (n=4) per group. ap<0.001 vs. control; bp<0.01 vs. MPTP. Control represents the intact side of MPTP-intoxicated monkeys.

FIG. 3 (A-D). Oral maraviroc treatment inhibits the infiltration of CD8+ T cells into the nigra of hemiparkinsonian monkeys. Naïve female rhesus monkeys received a right intracarotid injection of MPTP. After 7 d of injection, monkeys displaying classical parkinsonian postures received maraviroc (1 mg/kg body wt/d) orally mixed with banana. MPTP group of monkeys also received normal banana as control. After 30 d of treatment, ventral midbrain sections were DAB-stained for CD8 (A, vessel; B, parenchyma). CD8-positive cells were counted in two nigral sections (C, within 100 μm around vessel; D, parenchyma within 100 to 200 μm around vessel) of each of four monkeys (n=4) per group. ap<0.001 vs. control; bp<0.01 vs. MPTP. Control represents the intact side of MPTP-intoxicated monkeys.

FIG. 4 (A-E). Oral maraviroc treatment inhibits glial inflammation in the SNpc of hemiparkinsonian monkeys. Monkeys displaying classical parkinsonian postures received maraviroc (1 mg/kg body wt/d) orally mixed with banana. After 30 d of treatment, nigral sections were double-labeled for Iba1 and iNOS (A) and GFAP and iNOS (B). Cells positive for Iba1 (C), GFAP (D) and iNOS (E) were counted using the olympus microsuite V software in two nigral sections (two images per slide) of each of four monkeys (n=4) per group. ap<0.001 vs. control; bp<0.001 vs MPTP; ns, not significant vs MPTP.

FIG. 5 (A-C). Oral maraviroc treatment decreases α-synucleinapathy in the nigra of hemiparkinsonian monkeys. Naïve female rhesus monkeys received a right intracarotid injection of MPTP. After 7 d of injection, monkeys displaying classical parkinsonian postures received maraviroc (1 mg/kg body wt/d) orally mixed with banana. MPTP group of monkeys also received normal banana as control. After 30 d of treatment, nigral (A) sections were double-labeled for TH and α-syn. Total area (B) and integrated density (C) of α-syn bodies were quantified in two sections (two images per section) of each of four monkeys per group. ap<0.001 vs control (MPTP-intact); bp<0.001 vs MPTP-lesion.

FIG. 6 (A-C). Oral maraviroc treatment protects dopaminergic neurons in the SNpc of hemiparkinsonian monkeys. Naïve female rhesus monkeys received a right intracarotid injection of MPTP. After 7 d of injection, monkeys displaying classical parkinsonian postures received maraviroc (1 mg/kg body wt/d) orally mixed with banana. MPTP group of monkeys also received normal banana as control. A) After 30 d of treatment, nigral sections were immunostained for TH. B) A magnified image of TH-stained SNpc is shown. C) Estimates of dopaminergic nigral cell number [MPTP, n=4; (MPTP+maraviroc), n=4] were performed bilaterally using an unbiased design-based counting method (optical fractionator, StereoInvestigator; Microbrightfield, Williston, VT). All counting were performed by a single investigator blinded to the experimental conditions. ap<0.001 vs MPTP-intact; bp<0.01 vs MPTP-lesion.

FIG. 7 (A-B). Oral maraviroc treatment protects THir fibers in the striatum of hemiparkinsonian monkeys. Naïve female rhesus monkeys received a right intracarotid injection of MPTP. After 7 d of injection, monkeys displaying classical parkinsonian postures received maraviroc (1 mg/kg body wt/d) orally mixed with banana. MPTP group of monkeys also received normal banana as control. A) After 30 d of treatment, striatal sections were immunostained for TH. B) Optical density of TH fibers in caudate and putamen was calculated by digital image analysis. Six different striatal sections of each monkey were analyzed. ap<0.001 vs MPTP-intact; bp<0.01 vs MPTP-Caudate-lesion; cp<0.01 vs MPTP-Putamen-lesion.

FIG. 8 (A-E). Maraviroc protects striatal dopamine in hemiparkinsonian monkeys. Naïve female rhesus monkeys received a right intracarotid injection of MPTP. After 7 d of injection, monkeys displaying classical parkinsonian postures received maraviroc (1 mg/kg body wt/d) orally mixed with banana. MPTP group of monkeys also received normal banana as control. After 30 d of treatment, dopamine levels were measured in dorsomedial caudate (A), ventromedial caudate (B), dorsal putamen (C), ventral putamen (D), and nucleus accumbens (E). HPLC quantification of dopamine was performed by a single investigator blinded to the experimental conditions. Data are means±SEM of four monkeys per group. ap<0.001 vs MPTP-intact; bp<0.001 vs MPTP-lesion.

FIG. 9 (A-E). Maraviroc protects striatal DOPAC and HVA in hemiparkinsonian monkeys. Naïve female rhesus monkeys received a right intracarotid injection of MPTP. After 7 d of injection, monkeys displaying classical parkinsonian postures received maraviroc (1 mg/kg body wt/d) orally mixed with banana. MPTP group of monkeys also received normal banana as control. After 30 d of treatment, levels of DOPAC and HVA were measured in dorsomedial caudate (A), ventromedial caudate (B), dorsal putamen (C), ventral putamen (D), and nucleus accumbens (E). HPLC quantification of DOPAC and HVA was performed by a single investigator blinded to the experimental conditions. Data are means±SEM of four monkeys per group. ap<0.001 vs MPTP-intact; bp<0.001 vs MPTP-lesion; cp<0.05 vs MPTP-lesion.

DETAILED DESCRIPTION OF THE PREFERRED EMBODIMENTS

Definitions

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention.

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as", "for example") provided herein, is intended merely to better illuminate the invention and does not pose a limitation on the scope of the invention unless otherwise claimed. No language in the specification should be construed as indicating any non-claimed element as essential to the practice of the invention.

The term "therapeutic effect" as used herein means an effect which induces, ameliorates or otherwise causes an improvement in the pathological symptoms, disease progression or physiological conditions associated with or resistance to succumbing to a disorder, for example a neurological disease, of a human or veterinary subject. The term "therapeutically effective amount" as used with respect to a drug means an amount of the drug which imparts a therapeutic effect to the human or veterinary subject.

Compositions and Methods for Treating a Neurological Disorder.

The present invention generally relates to a method for treating a neurological disorder in a subject. The subject may be a human subject. In one embodiment, the method includes administering to the subject in need of such treatment a composition including a therapeutically effective amount of a CCR5 antagonist. In various embodiments, the CCR5 antagonist is maraviroc, aplaviroc, cenicriviroc or vicriviroc. In one preferred embodiment, the CCR5 antagonist is maraviroc. The therapeutically effective amount may be an amount that reduces or prevents intracytoplasmic aggregation of alpha-synuclein protein.

In one embodiment, the neurological disorder is characterized by an upregulation of at least one of the RANTES and eotaxin chemokines. The neurological disorder may be, for example, Alzheimer's disease, Parkinson's disease (PD), dementia with Lewy bodies and multiple system atrophy. In one preferred embodiment, the neurological disorder is Parkinson's disease.

The methods of treatment disclosed herein may include any number of modes of administering the CCR5 antagonist, for example maraviroc, aplaviroc, cenicriviroc or vicriviroc, or a pharmaceutical composition including the CCR5 antagonist. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixers, solid emulsions, solid dispersions or dispersible powders. For the preparation of pharmaceutical compositions for oral administration, the CCR5 antagonist may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. GELUCIRE). In the pharmaceutical composition, the CCR5 antagonist may also be dispersed in a microparticle, e.g. a nanoparticulate, composition.

For parenteral administration, the CCR5 antagonist or pharmaceutical compositions of the CCR5 antagonist can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration the agent or pharmaceutical compositions of the agent can be in the form of an aqueous, lipid, oily or other kind of solution or suspension or even administered in the form of liposomes or nano-suspensions.

In the treatment methods contemplated by the present disclosure, the CCR5 antagonist may be used alone or in compositions together with a pharmaceutically acceptable carrier or excipient. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Other suitable pharmaceutically acceptable excipients are described in "Remington's Pharmaceutical Sciences," Mack Pub. Co., New Jersey, 1991, the contents of which are expressly incorporated herein by reference.

In certain embodiments, the CCR5 antagonist may be orally administered to humans and other animals. The CCR5 antagonist may be formulated for administration and methods of formulation are well known in the art (see, for example, Remington: The Science and Practice of Pharmacy, Mack Publishing Company, Easton, Pa., 19th Edition (1995)).

In some embodiments, the formulations may be sustained-release formulations, meaning that they release the CCR5 antagonist steadily over an extended period of time. In other embodiments, the formulations may be delayed-release formulations, meaning that they release the CCR5 antagonist at a time later than that immediately following its administration.

Pharmaceutical compositions for use in accordance with the present disclosure can be in the form of sterile, non-pyrogenic liquid solutions or suspensions, coated capsules, lyophilized powders, or other forms known in the art.

Solid dosage forms for oral administration include capsules, tablets, pills, powders, and granules. In such solid dosage forms, the CCR5 antagonist is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the CCR5 antagonist only, or preferentially, in a certain part of the intestinal tract, optionally, in a delayed manner. Examples of embedding compositions that can be used include polymeric substances and waxes.

The CCR5 antagonist can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the CCR5 antagonist may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the CCR5 antagonist only, or preferentially, in a certain part of the intestinal tract, optionally, in a delayed manner. Examples of embedding compositions that can be used include polymeric substances and waxes.

Liquid dosage forms for oral administration include pharmaceutically acceptable emulsions, microemulsions, solutions, suspensions, syrups and elixirs. In addition to the CCR5 antagonist, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1,3 butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

The "therapeutically effective amount" or dose of CCR5 antagonist to be administered to warm-blooded animals, such as humans, may vary depending upon the neurological disorder to be treated. In some embodiments, the formulations are administered orally to the patient. In some embodiments, the total daily dose is delivered in a single administration. In other embodiments, the daily dose is divided into multiple doses, such as two or three substantially equal doses, and administered at different times throughout a day. In some embodiments, for the treatment of a neurological disorder, such as Parkinson's disease, a CCR5 antagonist is administered at a total daily dose of less than 200, 150, 100, 50, 25, 10, 5, 1, 0.5 or 0.1 mg/kg body weight.

EXAMPLES

Example 1: Reagents

Maraviroc was purchased from Selleck Chemicals (Houston, TX). Mouse anti-TH antibody (Immunostar), rabbit anti-α-syn antibody (clone: MJFR1) (Abcam), anti-CD4 antibody (Thermofisher), anti-CD8 antibody (Thermofisher), anti-Iba1 antibody (Abcam), anti-GFAP antibody (Agilent), and mouse anti-iNOS antibody (BD Bioscience) were purchased from different vendors. Cy2- and Cy5-conjugated secondary antibodies were obtained from Jackson Immuno Research Laboratories (West Grove, PA).

Example 2: Subjects and MPTP Intoxication

Female rhesus monkeys (6-8 years old; 5-7 kg) were used in this study. All animals were singly housed with a 12-h light/dark cycle. Purine monkey chow and water were available ad libitum. Diets were supplemented with fruit during the testing sessions. The study was performed in accordance with federal guidelines of proper animal care and with the approval of the IACUC. Monkeys were intoxicated with MPTP according to protocol described previously (12-16). Briefly, animals were tranquilized with ketamine (10 mg/kg, i.m.) and then maintained on an anesthetic plane with isoflurane (1-2%). The animals were put in the supine position. For each injection, a right-sided incision was made along the medial edge of the sternocleidomastoid muscle. The carotid sheath was opened and the common carotid artery, internal jugular vein, and vagus nerves were identified. The common carotid was exposed below the carotid bifurcation. The external carotid artery was then ligated. A 27 gauge butterfly needle was inserted into the common carotid artery in a direction retrograde to blood flow; for each injection, 20 ml of saline containing 3 mg of MPTP-HCl (Sigma) was infused at a rate of 1.33 ml/min (15 min). After the infusion was completed, 3 ml of saline was delivered, and then the incision was closed.

Example 3: Treatment of Hemiparkinsonian Monkeys by Maraviroc

Figure 1:
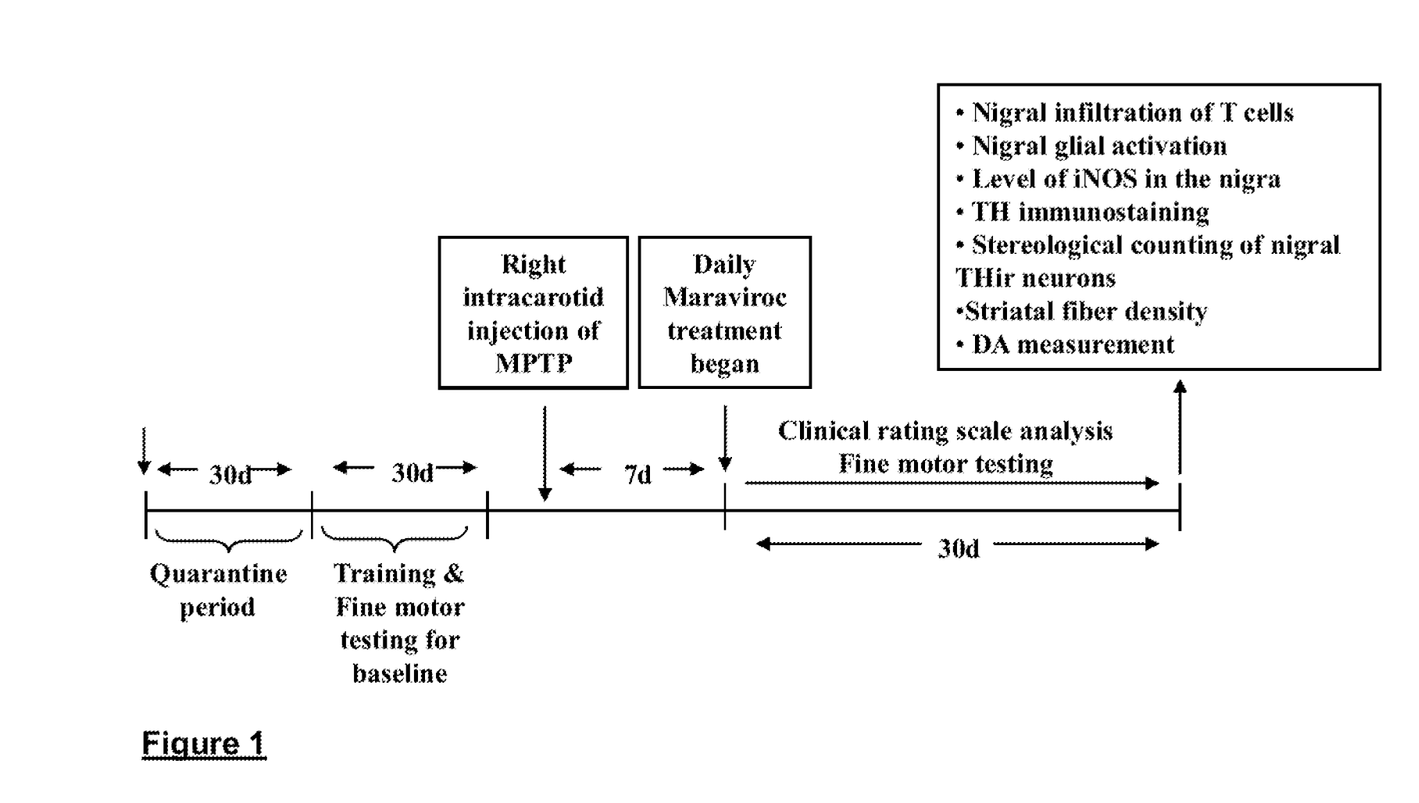
FIG. 1. Is a schematic presentation of experiments.

Monkeys displaying hemiparkinsonian symptoms 7 d after the first intracarotid injection were included in the study. Therefore, hemiparkinsonian monkeys were randomized and one group of hemiparkinsonian monkeys (n=4) were treated with maraviroc (1.0 mg/kg body wt/d) orally for 30 d through banana starting from 7 d of MPTP injection (FIG. 1). The control group of hemiparkinsonian monkeys (n=4) received only banana as vehicle.

Example 4: Immunohistochemistry

At the end point, monkeys were anesthetized with pentobarbital (25 mg/kg intravenously) and killed via perfusion with 0.9% saline. The brain was removed, immersed in ice-cold saline for 10 min, and slabbed on a monkey brain slicer (12, 13, 15, 16). Slabs through the head of the caudate and putamen were punched bilaterally with a 1-mm brain punch. These punches were processed for HPLC analysis (for quantification of neurotransmitters). Tissue slabs were immersed in Zamboni's fixative followed by immersion in 30% sucrose in PBS. Slabs were sectioned frozen (40 μm) on a sliding knife microtome. Tissue sections were stored in a cryoprotectant solution at 4° C. before use. For TH staining, midbrain sections were immunostained with mouse monoclonal anti-TH antibody (Immunostar and visualized by using DAB/H2O2 (DAB kit, Vector Laboratories) as described (13, 15, 17, 18).

Estimates of dopaminergic nigral cell number were performed bilaterally by an investigator blind to the treatment groups using an unbiased design-based counting method (optical fractionator, StereoInvestigator; Microbrightfield, Williston, VT). All counts were performed by a single investigator blinded to the experimental conditions. Using a random start, we outlined the substantia nigra under low magnification (1.25× objective) and sampled 20% of the treated nigra or 5% of the intact nigra in a random but systematic manner. Quantitation of striatal TH immunostaining was performed as previously described (15, 17, 18). Optical density measurements were obtained by digital image analysis (Scion, Frederick, MD).

For immunofluorescence staining, anti-Iba-1 antibody (1:500), anti-iNOS antibody (1:1000), and anti-GFAP antibody (1:1000) were used. The samples were mounted and observed under an Olympus IX81 fluorescence microscope as described before (17-19).

Example 5: HPLC Analysis

Samples were analyzed for neurotransmitters by an investigator blind to the treatment groups. On the day of the analysis, striatal tissues were sonicated in 0.2M perchloric acid containing isoproterenol (internal standard) and resulting homogenates were centrifuged at 20,000×g for 15 min at 4 C. After pH adjusting and filtration, 10 µl of supernatant was injected onto a Eicompak SC-3ODS column (HPLC-ECD System EiCOMHTEC-500 from JM Science Inc., Grand Island, NY) and levels of dopamine, 3, 4-dihydroxyphenylacetic acid (DOPAC) and homovanillic acid (HVA) were analyzed as described earlier (13, 17, 18, 20).

Example 6: Behavioral Analysis

The animals were trained to a consistent level of performance before intracarotid injection of MPTP. Monkeys were rated thrice a week by an investigator blind to the treatment groups using a parkinsonian rating scale (PD scale) utilized to quantify the clinical status of the monkeys (13-16). The scale included ratings of 10 parkinsonian features (tremor, posture, locomotion, hypokinesia, bradykinesia, balance, fine and gross motor skills, startle response, and freezing). Each test consisted of twelve total trials alternating between arms, six per side. Delaying feeding time until after the task was completed ensured animals' compliance with the test. Data collected included the time taken for the animal to move its hand into the chamber where the fruit was located (reaction time), the time taken to pick up the fruit while the hand was in the chamber (reception time) and the total time taken to move the hand into the chamber, retrieve the fruit and bring the hand back out of the panel and into the cage (total time).

Example 7: Statistical Analysis

All values are expressed as means±SEM. Differences among means were analyzed by one-way ANOVA or Kruskal-Wallis test (comparison among all groups) and post-hoc pair-wise comparison. In other cases, two sample t tests were also used to compare control vs MPTP and MPTP vs MPTP+maraviroc. For behavioral analysis, one way repeated measure ANOVA models were used. Pair-wise comparisons were conducted with Bonferroni adjustment.

Figure 2:
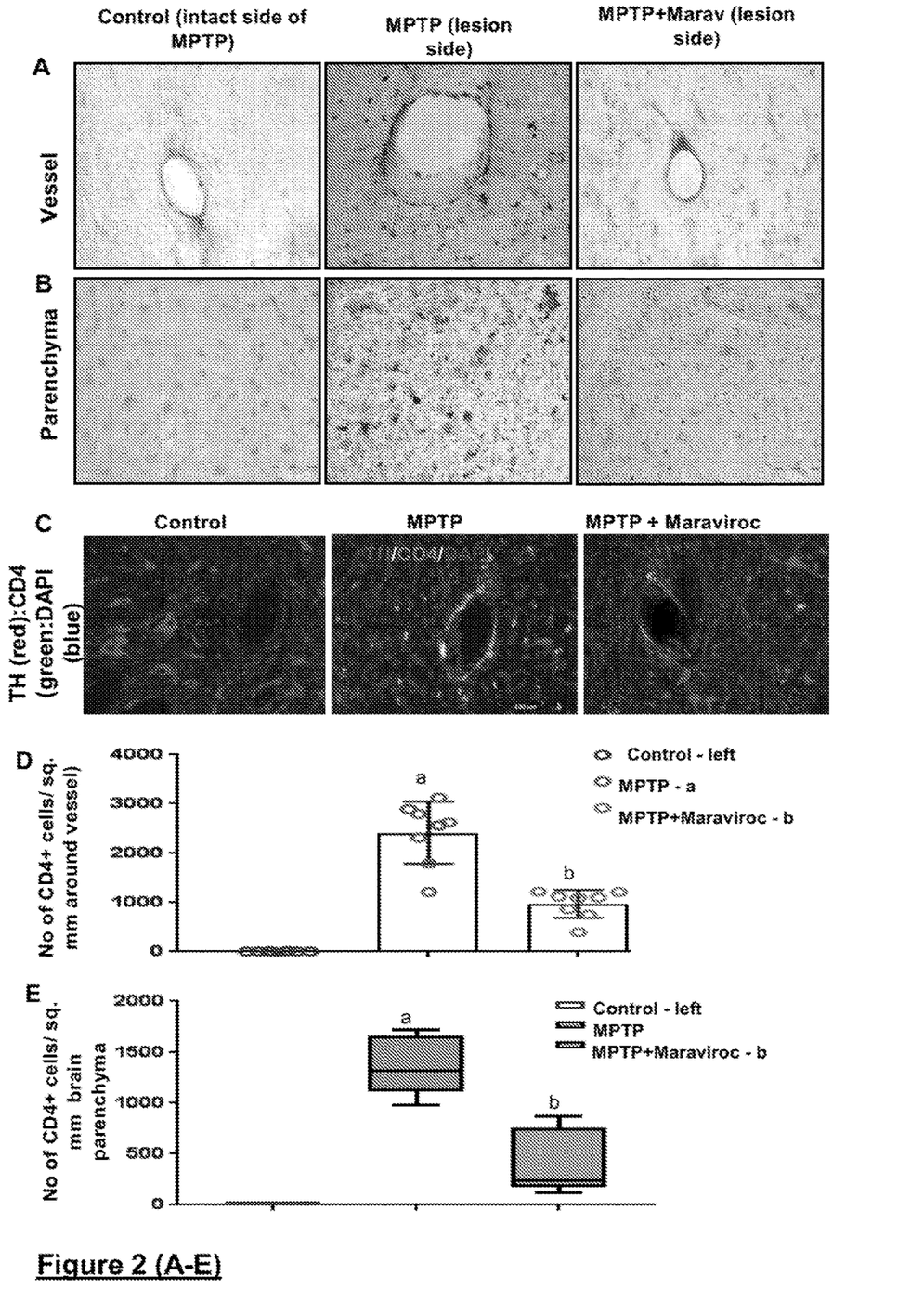
Figure 3:
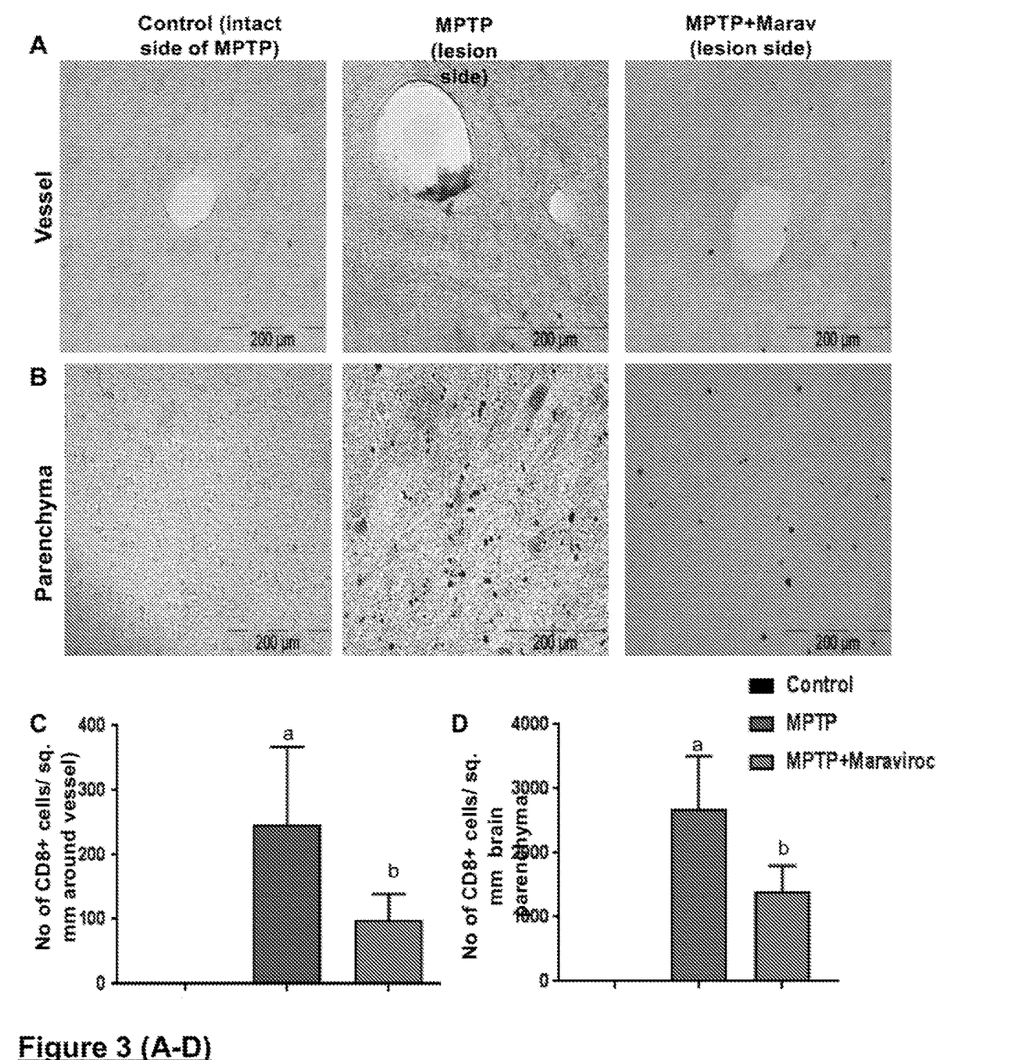

Example 8: Low Dose of Oral Maraviroc Inhibits the Infiltration of T Cells into the Nigra of Hemiparkinsonian Monkeys Similar to that seen in the nigra of postmortem PD brains, recently we reported that T cells also infiltrate into the nigra of hemiparkinsonian monkeys, the best available animal model of human PD (12). Since levels of RANTES and eotaxin, chemokines that are involved in T cell trafficking, are markedly increased in hemiparkinsonian monkeys (12) and maraviroc is an antagonist of CCR5, the receptor through which both RANTES and eotaxin function, we examined the efficacy of maraviroc on the infiltration of T cells into the nigra of hemiparkinsonian monkeys. Since in contrast to AIDS, virus is not involved in the pathogenesis of PD and the degree of T cell infiltration is also less in the CNS of PD patients as compared to HIV-associated dementia, we used low dose of maraviroc for treating hemiparkinsonian monkeys. Moreover, in order to make our primate work relevant to the clinical scenario, monkeys with established hemiparkinsonian symptoms were treated with maraviroc orally (FIG. 1). CD4 immunostaining (FIG. 2A-B, DAB staining; FIG. 2C, TH & CD4 double-labeling) clearly shows a typical CD4-immunoreactive inflammatory cuffing in the nigra of hemiparkinsonian, but not control, monkeys. Similarly, we also observed infiltration of CD8+ T cells into the nigra of hemiparkinsonian, but not control, monkeys (FIG. 3A-B). Although, CD4+ T cells (FIG. 2) were found to be more abundant than CD8+ T cells (FIG. 3) near blood vessel, more CD8+ T cells were detected in the deep parenchyma far from the lumen of blood vessels (FIGS. 3B & D) in the nigra of MPTP-treated monkey brain. However, oral treatment with maraviroc significantly attenuated the infiltration of both CD4+ and CD8+ T cells near the blood vessel as well as in deep parenchyma (FIGS. 2-3) of ventral midbrain. These results suggest maraviroc treatment is capable of suppressing the infiltration of T cells.

Figure 4:
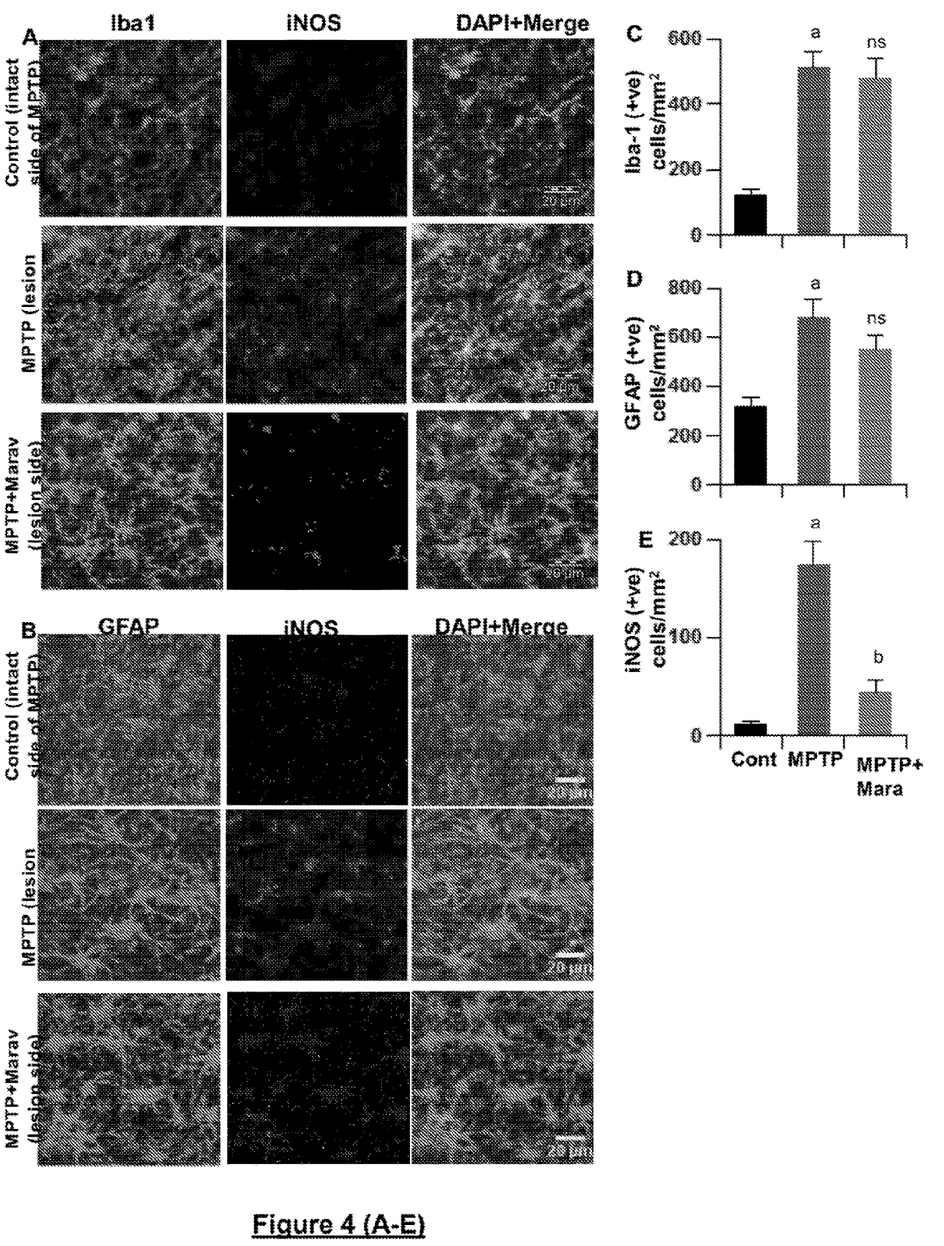

Example 9: Low Dose of Oral Maraviroc Suppresses Inflammation In Vivo in the Nigra of Hemiparkinsonian Monkeys It is becoming clear that neuroinflammation driven by glial cells (astrocytes and microglia) plays an important role in the loss of dopaminergic neurons in PD and its animal model (17, 18, 21-25). As reported earlier (13), MPTP intoxication led to marked increase in nigral iNOS protein expression in hemiparkinsonian monkeys. Consistent to the involvement of glial cells, this iNOS was mainly expressed by either Iba1-positive microglia (FIG. 4A) or GFAP-positive astrocytes (FIG. 48). However, oral maraviroc treatment reduced the expression of iNOS protein in the SNpc of hemiparkinsonian monkeys (FIGS. 4A, B & E). Similar to the increase in iNOS, we also observed increase in microglia and astrocytes in the SNpc of hemiparkinsonian monkeys (FIG. 4A-D). Interestingly, maraviroc treatment did not significantly reduce the number of astrocytes and microglia in the SNpc of hemiparkinsonian monkeys (FIG. 4A-D).

Figure 5:
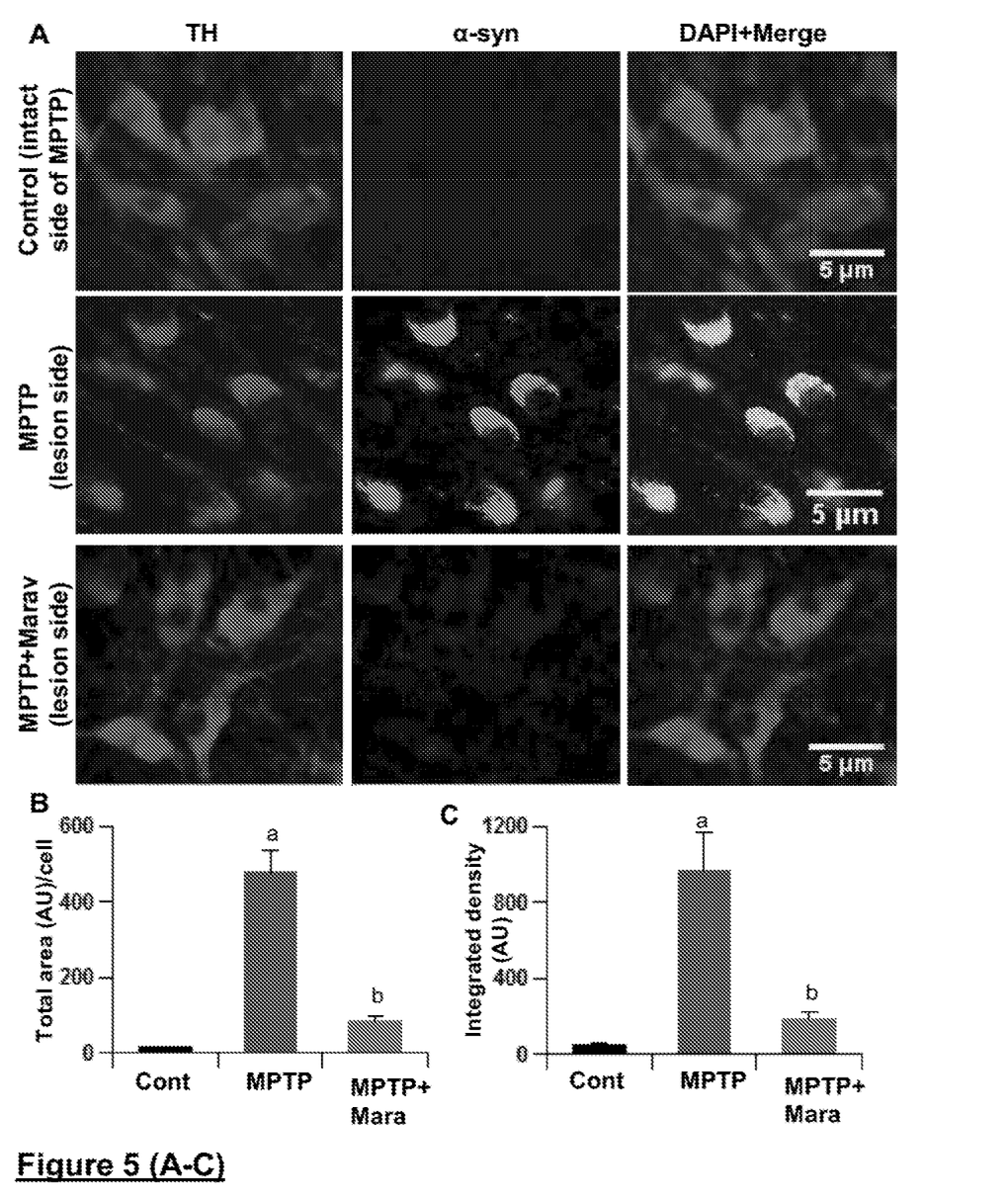

Example 10: Low-Dose Maraviroc Inhibits α-Synucleinopathy In Vivo in the Nigra of Hemiparkinsonian Monkeys Neuropathological hallmarks of PD are the presence of intracytoplasmic inclusions containing α-synuclein (α-syn) and the demise of dopaminergic neurons in the nigra. In addition to PD, accumulation of α-syn is also an important pathological hallmark of dementia with Lewy bodies (DLB) and multiple system atrophy (MSA) (26-28). Many in vitro and in vivo studies have shown that post-translational modifications of α-syn and associated protein aggregation are intimately coupled with neurotoxicity. Therefore, decreasing α-synucleinopathy may have therapeutic importance in PD and other Lewy body diseases. Accordingly, we observed widespread α-syn pathology in the nigra of monkeys after 37 d of MPTP intoxication (FIG. 5A-C). However, α-syn pathology was almost missing in the SNpc of hemiparkinsonian monkeys after oral maraviroc treatment (FIG. 5A-C).

Figure 6:
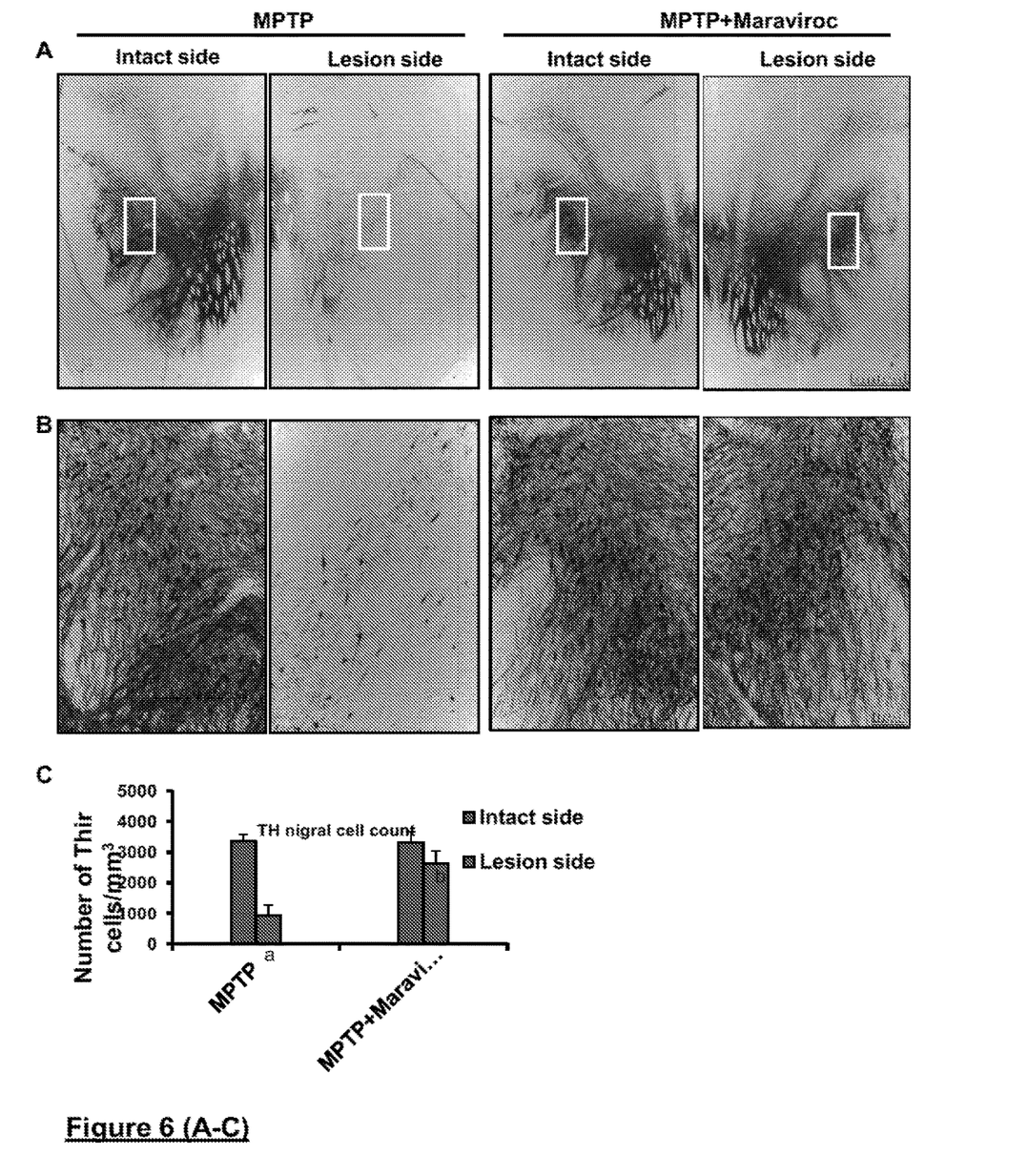
Figure 7:
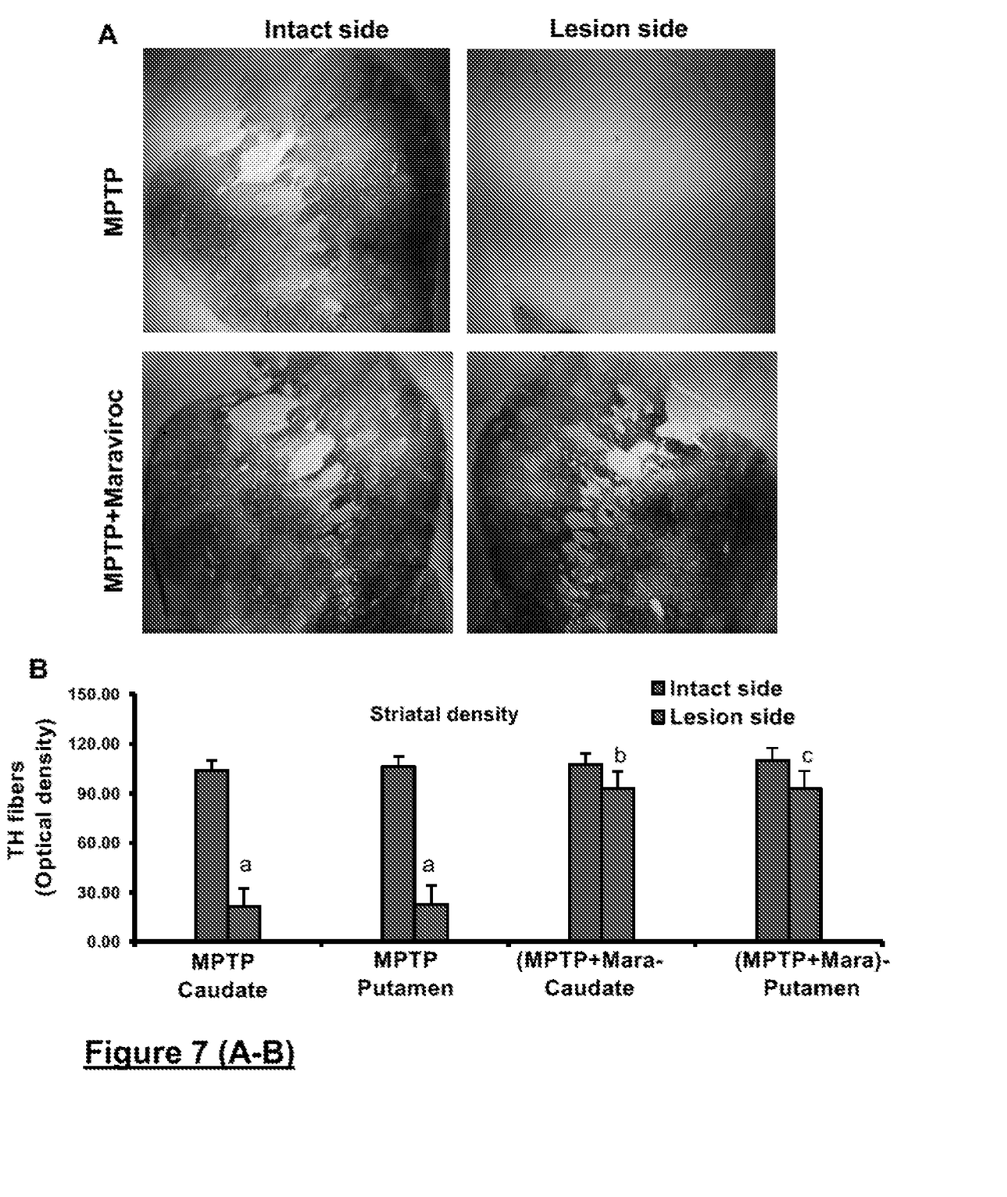
Figure 8:
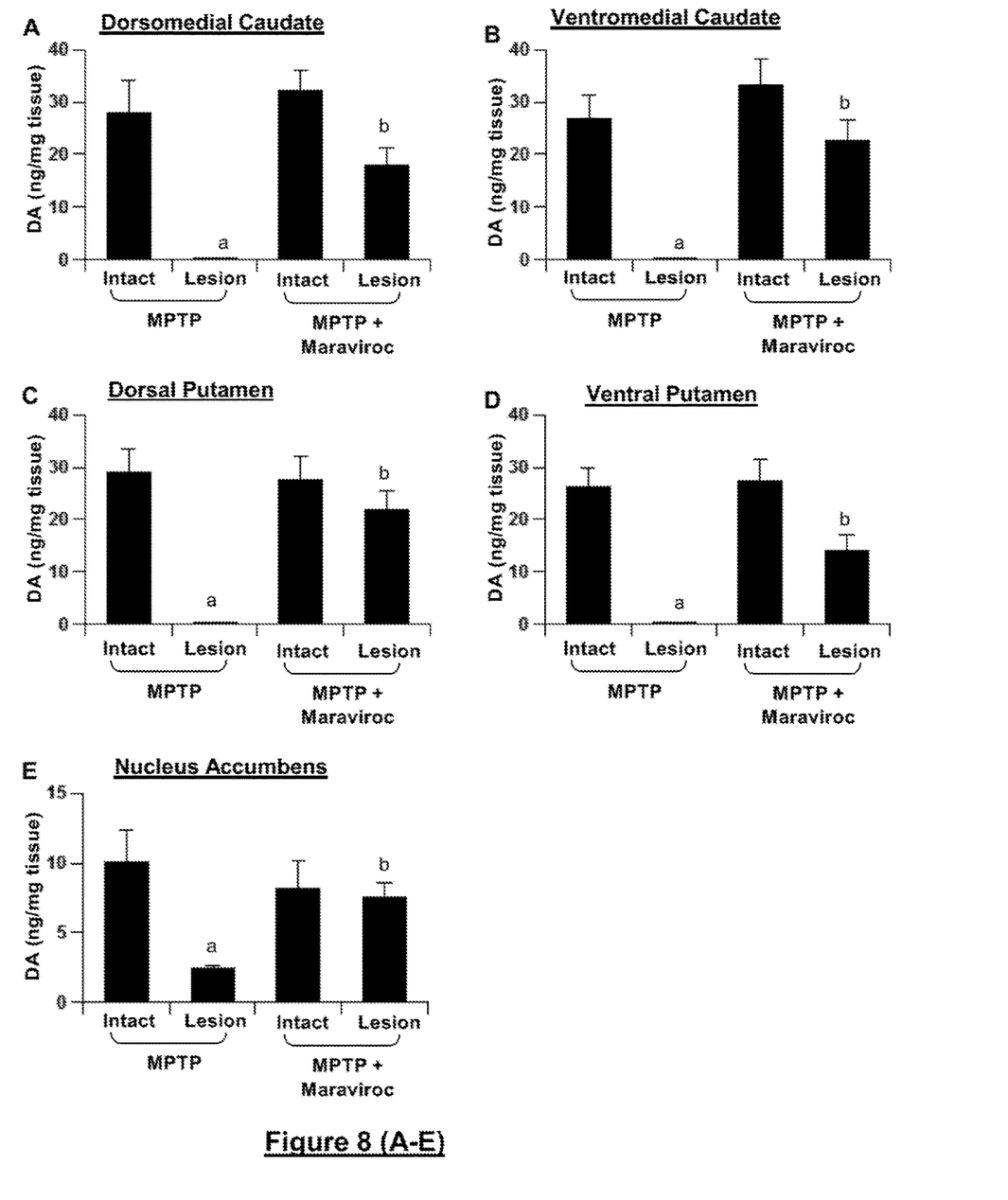
Figure 9:
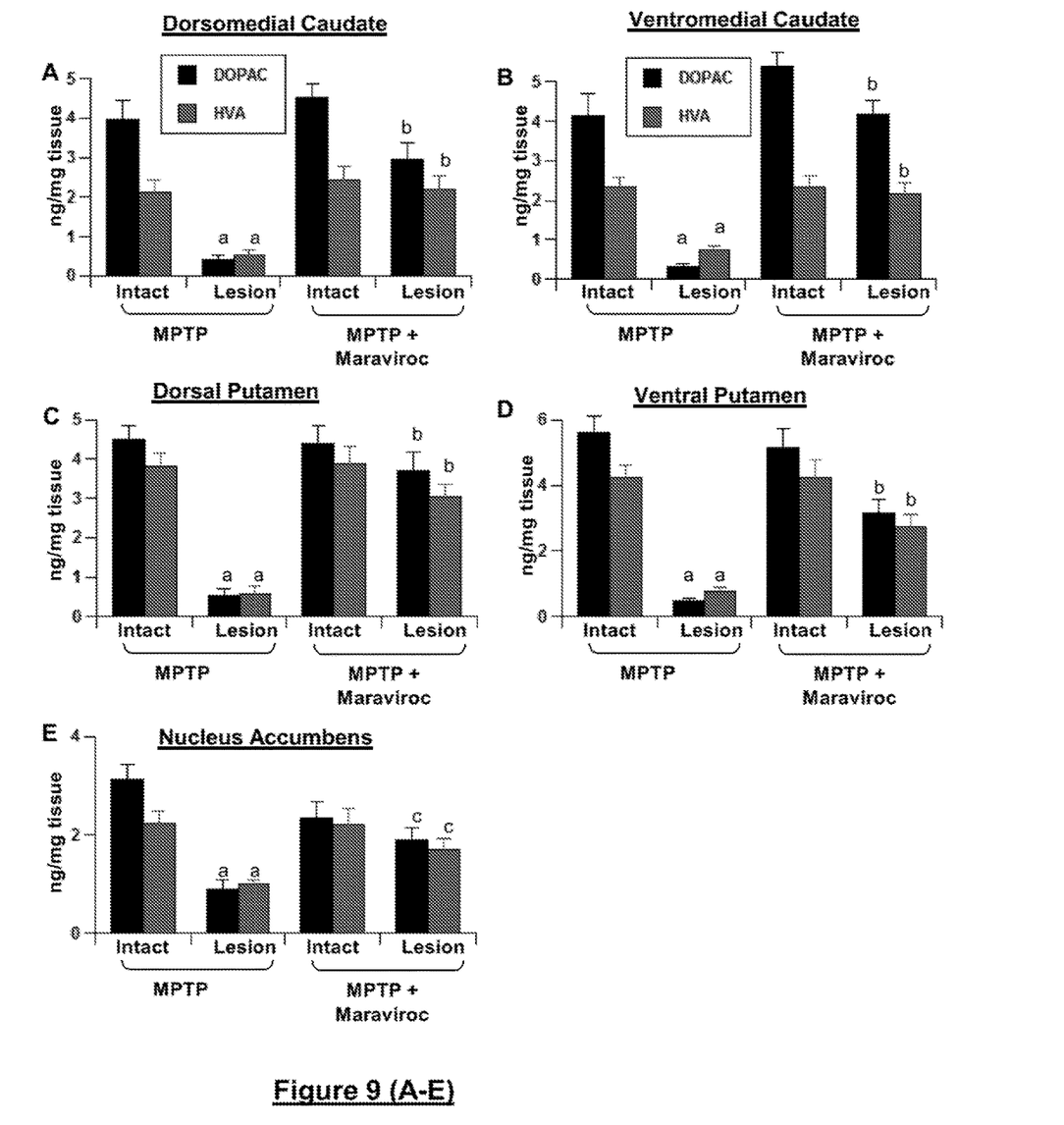

Example 11: Low-Dose Maraviroc Protects Dopamine Neurons and Fibers in Hemiparkinsonian Monkeys Since low-dose maraviroc treatment suppressed T cell infiltration into the nigra and inhibited glial activation as well as α-synucleinopathy in the nigra of MPTP-intoxicated mice, we examined the effect of maraviroc on nigrostriatal pathology. Therefore, after 30 d of treatment, animals were processed for quantification of dopaminergic cell bodies in the SNpc and of projecting dopaminergic fibers in the striatum using TH immunostaining. As expected, MPTP intoxication led to marked loss of nigral TH-positive neurons on 37 d of MPTP intoxication (FIG. 6A-B) compared with the intact side (control). Stereological counting of TH-ir neurons in nigral sections showed that MPTP-intoxication led to almost 80% loss of SNpc TH-positive neurons (FIG. 6C) in the lesion side compared with the control intact side. Similarly, quantitative measurements of optical density of the TH staining in caudate nucleus and putamen exhibited marked loss of striatal TH fibers (FIG. 7A-B) in the lesion side compared with the intact side. However, oral maraviroc treatment significantly restored SNpc TH-positive neurons (FIG. 6A-C) and striatal TH fibers (FIG. 7A-B) in hemiparkinsonian monkeys.

Example 12: Low-Dose Maraviroc Protects Striatal Neurotransmitters in Hemiparkinsonian Monkeys Since maraviroc protected dopaminergic neurons and fibers, next we determined if maraviroc also protected against biochemical deficits caused in hemiparkinsonian monkeys. Therefore, we quantified levels of dopamine (DA), 3,4-Dihydroxyphenylacetic acid (DOPAC) and homovanillic acid (HVA) in different parts of striatum. MPTP intoxication led to marked loss of DA in dorsomedial (FIG. 8A) and ventromedial caudate (FIG. 88), the dorsal (FIG. 8C) and ventral putamen (FIG. 8D), and the nucleus accumbens (FIG. 8E) of the lesion side compared to intact control side. In contrast, hemiparkinsonian monkeys that were treated with low-dose maraviroc exhibited pronounced preservation of DA in different parts of striatum (FIG. 8A-E). Similarly, maraviroc treatment also restored the levels of DOPAC and HVA in different parts of striatum of hemiparkinsonian monkeys (FIG. 9A-E).

Although maraviroc treatment displayed beneficial effects in hemiparkinsonian monkeys, it was important to know if this antiretroviral drug might evoke adverse effects on dopaminergic neurons in normal monkeys. However, in our unilateral model, we did not see any significant change in nigral dopaminergic neurons, striatal TH fiber density and striatal neurotransmitters in the intact side even after 30 d of maraviroc treatment, suggesting that maraviroc does not have detrimental effect on the normal nigrostriatum.

Example 13: Low-Dose Maraviroc Leads to Functional Improvement in Hemiparkinsonian Monkeys The eventual objective of any neuroprotective therapy is to decrease functional impairments. Therefore, monkeys were examined for performance on a hand reaching task, general activity, and clinical dysfunction (tremor, posture, locomotion, bradykinesia, balance, fine and gross motor skills, startle response, and freezing) based on a clinical rating scale modeled after the Unified Parkinson's Disease Rating Scale. As reported earlier (13-16), MPTP injection caused a marked decrease in performance in the left hand (contralateral to the MPTP infusion) while maintaining relatively normal function with the right hand (Table-1). However, oral maraviroc treatment significantly improved functional ability as observed on both a subjective clinical rating scale and an objective operant motor test (Table-1). Importantly, during maraviroc treatment, we did not observe any drug related side effect (e.g. hair loss, untoward infection, hyperkinesia, psychological disturbance, vomiting, diarrhea, etc.) in any of these monkeys.

Example 14: Discussion of Experimental Results

The applicant has determined that there is marked upregulation of RANTES and eotaxin, chemokines that are involved in the infiltration of T cells and other immune cells, in vivo in the SNpc and the serum of MPTP-intoxicated monkey (10). In another study, the applicant has demonstrated the upregulation of RANTES and eotaxin in the SNpc of postmortem PD brains as compared to age-matched controls (4). In MPTP mouse model as well, the applicant has found that RANTES and eotaxin are rapidly upregulated in nigra and serum and that functional blocking antibodies against RANTES and eotaxin protects mice against MPTP-induced nigrostriatal degeneration (4), suggesting that these chemokines play a role in dopamine neuron death.

While investigating the function of these chemokines, the applicant has found that a common receptor CCR5 is shared by both RANTES and eotaxin. Although different antagonists of CCR5 are available, maraviroc is the first member of the CCR5 antagonist class of antiretroviral medication, which has been approved for the treatment of HIV-1 infection by the FDA for use in combination with other antiretroviral agents. The applicant has demonstrated that oral administration of low-dose maraviroc reduces the infiltration of T cells into the nigra, attenuates nigral activation of glial cells, lowers α-syn pathology, protects dopaminergic neurons, normalizes striatal neurotransmitters, and improves motor functions in hemiparkinsonian monkeys.

Several lines of evidence demonstrate that oral maraviroc treatment results in protection of hemiparkinsonian monkeys both clinically and pathologically. These conclusions are based on the following. First, only the monkeys that exhibited parkinsonian posture, tremor and left hand freezing after intracarotid injection of MPTP were selected for maraviroc treatment. Second, chronic inflammation is a hallmark of PD pathology. Similarly, even after 37 d of single MPTP injection, levels of GFAP, Iba-1 and iNOS remained markedly higher in the lesioned nigra than non-lesioned nigra. However, oral maraviroc markedly reduced nigral expression of iNOS. This result was specific as there was not any significant inhibition in the number of GFAP-positive astroglia and Iba-1-positive microglia after maraviroc treatment. Third, α-syn accumulation is one of the hallmarks of both sporadic and familial PD (26-28), which is usually observed in hemiparkinsonian monkeys. However, maraviroc treatment markedly decreased α-syn pathology in the nigra of hemiparkinsonian monkeys. Fourth, as observed in PD, nigral dopaminergic neurons disappeared and the level of dopamine (DA) decreased in hemiparkinsonian monkeys. But treatment with maraviroc protected TH-positive dopaminergic neurons and restored the level of DA. Fifth, oral maraviroc also reversed motor deficits in a hand-reach task. Sixth, daily FDA-approved doses of maraviroc for adult HIV patients are 300 and 600 mg BID per patient. It is prescribed at a dose of 150 mg/d for baby HIV patients. However, in hemiparkinsonian monkeys, maraviroc markedly protected the nigrostriatum and improved locomotor activities at a much lower dose. A dose of 1 mg/kg body wt/d is equivalent to 70-80 mg QD per patient that is lower than even the baby dose of maraviroc. These results suggest that maraviroc may be effective in PD patients at very low doses.

The applicant has demonstrated that RANTES and eotaxin, chemokines that are involved in the infiltration of T cells and other immune cells, are upregulated in the SNpc and the serum of MPTP-intoxicated monkey (10). These two chemokines are also upregulated in vivo in the SNpc of postmortem PD brains as compared to age-matched controls (4). According to Tang et al (39), serum RANTES levels strongly correlated with Hoehn-Yahr score and disease duration in PD patients. Interestingly, both RANTES and eotaxin share the same receptor CCR5, which is inhibited by maraviroc. CCR5-mediated T cell infiltration into the target organ occurs during many pathological conditions including HIV infection and cancer (40, 41). By antagonizing CCR5, maraviroc inhibits the infiltration of T cells T cells in HIV infection and cancer. As observed in the nigra of PD patients (8), both CD8+ and CD4+ T cells significantly invaded into the nigra of hemiparkinsonian monkeys. There are several direct and indirect pathways by which T cell infiltration could influence dopaminergic neurodegeneration. For example, it has been reported that the migration of antigen-specific CD4+ T cells from the periphery to the CNS generates immunocyte-microglial activities that perpetuate neuroinflammation and affect neuronal survival (42). Earlier we have shown that effector T cells are capable of activating microglia for the production of various proinflammatory molecules via cell-to-cell contact (43, 44). This contact process involves VLA4 (α4β1) integrin of T cells and VCAM1 of microglia (44, 45). Furthermore, activated T cells may also activate microglia via CD40-CD40 ligation (7, 9, 11). According to Nitsch et al (10), cytotoxic T cell-mediated lethal increase in neuronal calcium could be prevented by blocking both perforin and glutamate receptors. Interestingly, oral administration of maraviroc strikingly suppressed the infiltration of CD8+ and CD4+ T cells into the nigra. Adaptive immune response can be driven by a number of mechanisms (46, 47). Here, the beauty of our finding is that antagonism of a particular component of the adaptive immune arm (CCR5) is sufficient to protect the loss of dopaminergic neurons, improve striatal DA, and reverse motor deficits in hemiparkinsonian monkeys.

REFERENCES

1. Vila, M., and S. Przedborski. 2004. Genetic clues to the pathogenesis of Parkinson's disease. Nat Med 10 Suppl: S58-62.
2. Olanow, C. W., and W. G. Tatton. 1999. Etiology and pathogenesis of Parkinson's disease. Annu Rev Neurosci 22:123-144.
3. Dauer, W., and S. Przedborski. 2003. Parkinson's disease: mechanisms and models. Neuron 39:889-909.
4. Chandra, G., S. B. Rangasamy, A. Roy, J. H. Kordower, and K. Pahan. 2016. Neutralization of RANTES and Eotaxin Prevents the Loss of Dopaminergic Neurons in a Mouse Model of Parkinson Disease. J Biol Chem 291: 15267-15281.
5. Chandra, G., A. Roy, S. B. Rangasamy, and K. Pahan. 2017. Induction of Adaptive Immunity Leads to Nigrostriatal Disease Progression in MPTP Mouse Model of Parkinson's Disease. J Immunol 198:4312-4326.
6. Sulzer, D., R. N. Alcalay, F. Garretti, L. Cote, E. Kanter, J. Agin-Liebes, C. Liong, C. McMurtrey, W. H. Hildebrand, X. Mao, V. L. Dawson, T. M. Dawson, C. Oseroff, J. Pham, J. Sidney, M. B. Dillon, C. Carpenter, D. Weiskopf, E. Phillips, S. Mallal, B. Peters, A. Frazier, C. S. Lindestam Arlehamn, and A. Sette. 2017. T cells from patients with Parkinson's disease recognize alpha-synuclein peptides. Nature 546:656-661.
7. Jana, M., S. Dasgupta, X. Liu, and K. Pahan. 2002. Regulation of tumor necrosis factor-alpha expression by CD40 ligation in BV-2 microglial cells. J Neurochem 80:197-206.
8. Brochard, V., B. Combadiere, A. Prigent, Y. Laouar, A. Perrin, V. Beray-Berthat, O. Bonduelle, D. Alvarez-Fischer, J. Callebert, J. M. Launay, C. Duyckaerts, R. A. Flavell, E. C. Hirsch, and S. Hunot. 2009. Infiltration of CD4+ lymphocytes into the brain contributes to neurodegeneration in a mouse model of Parkinson disease. J Clin Invest 119:182-192.
9. Chabot, S., D. Charlet, T. L. Wilson, and V. W. Yong. 2001. Cytokine production consequent to T cell-microglia interaction: the PMA/IFN gamma-treated U937 cells display similarities to human microglia. J Neurosci Methods 105:111-120.
10. Nitsch, R., E. E. Pohl, A. Smorodchenko, C. Infante-Duarte, O. Aktas, and F. Zipp. 2004. Direct impact of T cells on neurons revealed by two-photon microscopy in living brain tissue. J Neurosci 24:2458-2464.
11. Jana, M., X. Liu, S. Koka, S. Ghosh, T. M. Petro, and K. Pahan. 2001. Ligation of CD40 stimulates the induction of nitric-oxide synthase in microglial cells. J Biol Chem 276:44527-44533.
12. Roy, A., S. Mondal, J. H. Kordower, and K. Pahan. 2015. Attenuation of microglial RANTES by NEMO-binding domain peptide inhibits the infiltration of CD8(+) T cells in the nigra of hemiparkinsonian monkey. Neuroscience 302:36-46.
13. Mondal, S., A. Roy, A. Jana, S. Ghosh, J. H. Kordower, and K. Pahan. 2012. Testing NF-kappaB-based therapy in hemiparkinsonian monkeys. J Neuroimmune Pharmacol 7:544-556.
14. Emborg, M. E., P. Shin, B. Roitberg, J. G. Sramek, Y. Chu, G. T. Stebbins, J. S. Hamilton, P. D. Suzdak, J. P. Steiner, and J. H. Kordower. 2001. Systemic administration of the immunophilin ligand GPI 1046 in MPTP-treated monkeys. Exp Neurol 168:171-182.
15. Kordower, J. H., M. E. Emborg, J. Bloch, S. Y. Ma, Y. Chu, L. Leventhal, J. McBride, E. Y. Chen, S. Palfi, B. Z. Roitberg, W. D. Brown, J. E. Holden, R. Pyzalski, M. D. Taylor, P. Carvey, Z. Ling, D. Trono, P. Hantraye, N. Deglon, and P. Aebischer. 2000. Neurodegeneration prevented by lentiviral vector delivery of GDNF in primate models of Parkinson's disease. Science 290:767-773.
16. Kordower, J. H., C. D. Herzog, B. Dass, R. A. Bakay, J. Stansell, 3rd, M. Gasmi, and R. T. Bartus. 2006. Delivery of neurturin by AAV2 (CERE-120)-mediated gene transfer provides structural and functional neuroprotection and neurorestoration in MPTP-treated monkeys. Ann Neurol 60:706-715.

17. Ghosh, A., A. Roy, X. Liu, J. H. Kordower, E. J. Mufson, D. M. Hartley, S. Ghosh, R. L. Mosley, H. E. Gendelman, and K. Pahan. 2007. Selective inhibition of NF-kappaB activation prevents dopaminergic neuronal loss in a mouse model of Parkinson's disease. Proc Natl Acad Sci USA 104:18754-18759.
18. Ghosh, A., A. Roy, J. Matras, S. Brahmachari, H. E. Gendelman, and K. Pahan. 2009. Simvastatin inhibits the activation of p21 ras and prevents the loss of dopaminergic neurons in a mouse model of Parkinson's disease. J Neurosci 29:13543-13556.
19. Khasnavis, S., and K. Pahan. Sodium Benzoate, a Metabolite of Cinnamon and a Food Additive, Upregulates Neuroprotective Parkinson Disease Protein DJ-1 in Astrocytes and Neurons. J Neuroimmune Pharmacol 7:424-435.
20. Roy, A., and K. Pahan. Prospects of statins in Parkinson disease. Neuroscientist 17:244-255.
21. Mogi, M., M. Harada, H. Narabayashi, H. Inagaki, M. Minami, and T. Nagatsu. 1996. Interleukin (IL)-1 beta, IL-2, IL-4, IL-6 and transforming growth factor-alpha levels are elevated in ventricular cerebrospinal fluid in juvenile parkinsonism and Parkinson's disease. Neurosci Lett 211:13-16.
22. Nagatsu, T., M. Mogi, H. Ichinose, and A. Togari. 2000. Changes in cytokines and neurotrophins in Parkinson's disease. J Neural Transm Suppl:277-290.
23. Qureshi, G. A., S. Baig, I. Bednar, P. Sodersten, G. Forsberg, and A. Siden. 1995. Increased cerebrospinal fluid concentration of nitrite in Parkinson's disease. Neuroreport 6:1642-1644.
24. Dehmer, T., J. Lindenau, S. Haid, J. Dichgans, and J. B. Schulz. 2000. Deficiency of inducible nitric oxide synthase protects against MPTP toxicity in vivo. J Neurochem 74:2213-2216.
25. Gao, H. M., B. Liu, W. Zhang, and J. S. Hong. 2003. Novel anti-inflammatory therapy for Parkinson's disease. Trends Pharmacol Sci 24:395-401.
26. Volpicelli-Daley, L. A., K. C. Luk, and V. M. Lee. 2014. Addition of exogenous alpha-synuclein preformed fibrils to primary neuronal cultures to seed recruitment of endogenous alpha-synuclein to Lewy body and Lewy neurite-like aggregates. Nat Protoc 9:2135-2146.
27. Goedert, M. 2001. Alpha-synuclein and neurodegenerative diseases. Nat Rev Neurosci 2:492-501.
28. Lashuel, H. A., C. R. Overk, A. Oueslati, and E. Masliah. 2013. The many faces of alpha-synuclein: from structure and toxicity to therapeutic target. Nat Rev Neurosci 14:38-48.
29. Kannarkat, G. T., J. M. Boss, and M. G. Tansey. 2014. The role of innate and adaptive immunity in Parkinson's disease. J Parkinsons Dis 3:493-514.
30. Hunot, S., and E. C. Hirsch. 2003. Neuroinflammatory processes in Parkinson's disease. Ann Neurol 53 Suppl 3:S49-58; discussion S58-60.
31. Khasnavis, S., A. Roy, S. Ghosh, R. Watson, and K. Pahan. 2014. Protection of dopaminergic neurons in a mouse model of Parkinson's disease by a physically-modified saline containing charge-stabilized nanobubbles. J Neuroimmune Pharmacol 9:218-232.
32. Laurie, C., A. Reynolds, O. Coskun, E. Bowman, H. E. Gendelman, and R. L. Mosley. 2007. CD4+ T cells from Copolymer-1 immunized mice protect dopaminergic neurons in the 1-methyl-4-phenyl-1,2,3,6-tetrahydropyridine model of Parkinson's disease. J Neuroimmunol 183:60-68.
33. Roy, A., A. Ghosh, A. Jana, X. Liu, S. Brahmachari, H. E. Gendelman, and K. Pahan. 2012. Sodium phenylbutyrate controls neuroinflammatory and antioxidant activities and protects dopaminergic neurons in mouse models of Parkinson's disease. PLoS One 7:e38113.
34. Wu, D. C., V. Jackson-Lewis, M. Vila, K. Tieu, P. Teismann, C. Vadseth, D. K. Choi, H. Ischiropoulos, and S. Przedborski. 2002. Blockade of microglial activation is neuroprotective in the 1-methyl-4-phenyl-1,2,3,6-tetrahydropyridine mouse model of Parkinson disease. J Neurosci 22:1763-1771.
35. Gibbs, R. A., J. Rogers, M. G. Katze, R. Bumgarner, G. M. Weinstock, E. R. Mardis, K. A. Remington, R. L. Strausberg, J. C. Venter, R. K. Wilson, M. A. Batzer, C. D. Bustamante, E. E. Eichler, M. W. Hahn, R. C. Hardison, K. D. Makova, W. Miller, A. Milosavljevic, R. E. Palermo, A. Siepel, J. M. Sikela, T. Attaway, S. Bell, K. E. Bernard, C. J. Buhay, M. N. Chandrabose, M. Dao, C. Davis, K. D. Delehaunty, Y. Ding, H. H. Dinh, S. Dugan-Rocha, L. A. Fulton, R. A. Gabisi, T. T. Garner, J. Godfrey, A. C. Hawes, J. Hernandez, S. Hines, M. Holder, J. Hume, S. N. Jhangiani, V. Joshi, Z. M. Khan, E. F. Kirkness, A. Cree, R. G. Fowler, S. Lee, L. R. Lewis, Z. Li, Y. S. Liu, S. M. Moore, D. Muzny, L. V. Nazareth, D. N. Ngo, G. O. Okwuonu, G. Pai, D. Parker, H. A. Paul, C. Pfannkoch, C. S. Pohl, Y. H. Rogers, S. J. Ruiz, A. Sabo, J. Santibanez, B. W. Schneider, S. M. Smith, E. Sodergren, A. F. Svatek, T. R. Utterback, S. Vattathil, W. Warren, C. S. White, A. T. Chinwalla, Y. Feng, A. L. Halpern, L. W. Hillier, X. Huang, P. Minx, J. O. Nelson, K. H. Pepin, X. Qin, G. G. Sutton, E. Venter, B. P. Walenz, J. W. Wallis, K. C. Worley, S. P. Yang, S. M. Jones, M. A. Marra, M. Rocchi, J. E. Schein, R. Baertsch, L. Clarke, M. Csuros, J. Glasscock, R. A. Harris, P. Havlak, A. R. Jackson, H. Jiang, Y. Liu, D. N. Messina, Y. Shen, H. X. Song, T. Wylie, L. Zhang, E. Birney, K. Han, M. K. Konkel, J. Lee, A. F. Smit, B. Ullmer, H. Wang, J. Xing, R. Burhans, Z. Cheng, J. E. Karro, J. Ma, B. Raney, X. She, M. J. Cox, J. P. Demuth, L. J. Dumas, S. G. Han, J. Hopkins, A. Karimpour-Fard, Y. H. Kim, J. R. Pollack, T. Vinar, C. Addo-Quaye, J. Degenhardt, A. Denby, M. J. Hubisz, A. Indap, C. Kosiol, B. T. Lahn, H. A. Lawson, A. Marklein, R. Nielsen, E. J. Vallender, A. G. Clark, B. Ferguson, R. D. Hernandez, K. Hirani, H. Kehrer-Sawatzki, J. Kolb, S. Patil, L. L. Pu, Y. Ren, D. G. Smith, D. A. Wheeler, I. Schenck, E. V. Ball, R. Chen, D. N. Cooper, B. Giardine, F. Hsu, W. J. Kent, A. Lesk, D. L. Nelson, E. O'Brien W, K. Prufer, P. D. Stenson, J. C. Wallace, H. Ke, X. M. Liu, P. Wang, A. P. Xiang, F. Yang, G. P. Barber, D. Haussler, D. Karolchik, A. D. Kern, R. M. Kuhn, K. E. Smith, and A. S. Zwieg. 2007. Evolutionary and biomedical insights from the rhesus macaque genome. Science 316:222-234.
36. Tanabe, Y., S. Sasaki, N. Mukaida, and T. Baba. 2016. Blockade of the chemokine receptor, CCR5, reduces the growth of orthotopically injected colon cancer cells via limiting cancer-associated fibroblast accumulation. Oncotarget 7:48335-48345.
37. Zi, J., S. Yuan, J. Qiao, K. Zhao, L. Xu, K. Qi, K. Xu, and L. Zeng. 2017. Treatment with the C—C chemokine receptor type 5 (CCR5)-inhibitor maraviroc suppresses growth and induces apoptosis of acute lymphoblastic leukemia cells. Am J Cancer Res 7:869-880.
38. Velasco-Velazquez, M., X. Jiao, M. De La Fuente, T. G. Pestell, A. Ertel, M. P. Lisanti, and R. G. Pestell. 2012. CCR5 antagonist blocks metastasis of basal breast cancer cells. Cancer Res 72:3839-3850.

39. Tang, P., L. Chong, X. Li, Y. Liu, P. Liu, C. Hou, and R. Li. 2014. Correlation between serum RANTES levels and the severity of Parkinson's disease. Oxid Med Cell Longev 2014:208408.
40. Velasco-Velazquez, M., W. Xolalpa, and R. G. Pestell. 2014. The potential to target CCL5/CCR5 in breast cancer. Expert Opin Ther Targets 18:1265-1275.
41. Gilliam, B. L., D. J. Riedel, and R. R. Redfield. 2011. Clinical use of CCR5 inhibitors in HIV and beyond. J Transl Med 9 Suppl 1:S9.
42. Gendelman, H. E., and R. L. Mosley. 2015. A Perspective on Roles Played by Innate and Adaptive Immunity in the Pathobiology of Neurodegenerative Disorders. J Neuroimmune Pharmacol 10:645-650.
43. Dasgupta, S., M. Jana, X. Liu, and K. Pahan. 2002. Myelin basic protein-primed T cells induce nitric oxide synthase in microglial cells. Implications for multiple sclerosis. J Biol Chem 277:39327-39333.
44. Dasgupta, S., M. Jana, X. Liu, and K. Pahan. 2003. Role of very-late antigen-4 (VLA-4) in myelin basic protein-primed T cell contact-induced expression of proinflammatory cytokines in microglial cells. J Biol Chem 278: 22424-22431.
45. Brahmachari, S., and K. Pahan. 2010. Gender-specific expression of beta1 integrin of VLA-4 in myelin basic protein-primed T cells: implications for gender bias in multiple sclerosis. J Immunol 184:6103-6113.
46. Iwasaki, A., and R. Medzhitov. 2015. Control of adaptive immunity by the innate immune system. Nat Immunol 16:343-353.
47. Iwasaki, A., and R. Medzhitov. 2010. Regulation of adaptive immunity by the innate immune system. Science 327:291-295.

TABLE 1

Oral Maraviroc treatment led to functional improvements in hemiparkinsonian monkeys.

| Motor parameters | Before MPTP infusion | After MPTP infusion | After treatment MPTP + banana + Maraviroc-banana | MPTP |
|---|---|---|---|---|
| General (Gross) motor skills (0-3) | | | | |
| R Hand | 0.00 ± 0.00 | 0.12 ± 0.01 | 0.07 ± 0.04 | 0.01 ± 0.00 |
| L Hand | 0.00 ± 0.00 | 1.93 ± 0.12 | 1.57 ± 0.88 | 0.89 ± 0.05 |
| Tremor (0-3) | | | | |
| R Hand | 0.00 ± 0.00 | 0.21 ± 0.03 | 0.00 ± 0.00 | 0.00 ± 0.00 |
| L Hand | 0.00 ± 0.00 | 1.24 ± 0.32 | 1.07 ± 0.70 | 0.42 ± 0.03[a] |
| Balance (0-3) | 0.00 ± 0.00 | 1.75 ± 0.28 | 1.59 ± 0.50 | 0.57 ± 0.04[a] |
| Posture (0-3) | 0.00 ± 0.00 | 1.50 ± 0.43 | 1.35 ± 0.50 | 0.39 ± 0.04[a] |
| Brady kinesia (0-5) | 0.00 ± 0.00 | 2.12 ± 0.32 | 1.97 ± 0.42 | 0.85 ± 0.28[a] |
| Gait (0-5) | 0.00 ± 0.00 | 1.75 ± 0.05 | 1.63 ± 0.83 | 0.25 ± 0.03[a] |
| Defense Reaction (0-2) | 0.96 ± 0.71 | 0.87 ± 0.14 | 0.75 ± 0.08 | 0.24 ± 0.07[a] |
| Freezing (0-2) | 0.00 ± 0.00 | 0.92 ± 0.14 | 0.81 ± 0.23 | 0.39 ± 0.03[a] |
| Total (Sum mean) | 0.96 ± 0.07 | 12.41 ± 1.23 | 10.81 ± 0.32 | 4.01 ± 0.40[a] |

Naïve female rhesus monkeys received a right intracarotid injection of MPTP. After 7 d of injection, monkeys displaying classical parkinsonian postures received maraviroc (1 mg/kg body wt/d) orally mixed with banana. MPTP group of monkeys also received normal banana as control. Monkeys were rated thrice a week using a parkinsonian rating scale (PD scale) utilized to quantify the clinical status of the monkeys. The scale included ratings of 10 parkinsonian features (tremor, posture, locomotion, hypokinesia, bradykinesia, balance, fine and gross motor skills, startle response, and freezing). Monkeys were not tested on these tasks during the week between MPTP intoxication and initiation of maraviroc treatment. Results are mean ± SEM of four monkeys per group. [a]$p < 0.001$ vs MPTP-banana.

I claim:

1. A method for treating a neurological disorder in a subject, the method comprising administering to the subject in need of such treatment a composition comprising a therapeutically effective amount of a CCR5 antagonist, wherein the CCR5 antagonist is maraviroc, aplaviroc, cenicriviroc or vicriviroc, wherein the neurological disorder is selected from the group consisting of Alzheimer's disease, dementia with Lewy bodies and multiple system atrophy.

2. The method of claim 1, wherein the CCR5 antagonist is maraviroc.

3. The method of claim 1, wherein the neurological disorder is Alzheimer's disease.

4. The method of claim 1, wherein the neurological disorder is dementia with Lewy bodies.

5. The method of claim 1, wherein the neurological disorder is multiple system atrophy.

6. The method of claim 1, wherein the neurological disorder is characterized by an upregulation of at least one of RANTES and eotaxin, chemokines.

7. The method of claim 1, wherein the composition reduces or prevents intracytoplasmic aggregation of alpha-synuclein protein.

8. The method of claim 1, wherein the composition further comprises at least one pharmaceutically acceptable carrier.

9. The method of claim 1, wherein the composition is administered orally.

10. The method of claim 1, wherein the composition is administered by a route selected from the group consisting of the subcutaneous, intra-articular, intradermal, intravenous, intraperitoneal and intramuscular routes.

11. The method of claim 1, wherein the subject is a human subject.

12. The method of claim 11, wherein the CCR5 antagonist is administrated orally in a daily amount of less than 200 mg/kg body weight of the human subject.

13. The method of claim 12, wherein the CCR5 antagonist is administrated orally in a daily amount of less than 10 mg/kg body weight of the human subject.

14. The method of claim 13, wherein the CCR5 antagonist is administrated orally in a daily amount of less than 1 mg/kg body weight of the human subject.

* * * * *